United States Patent
Banerjee et al.

(10) Patent No.: US 8,309,331 B2
(45) Date of Patent: Nov. 13, 2012

(54) SYSTEMS AND METHODS FOR ALTERING RATES OF ENZYMATIC PROCESSES

(75) Inventors: Sujit Banerjee, Marietta, GA (US); John T. Reye, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 102 days.

(21) Appl. No.: 12/809,361

(22) PCT Filed: Dec. 18, 2008

(86) PCT No.: PCT/US2008/087472
§ 371 (c)(1),
(2), (4) Date: Jun. 18, 2010

(87) PCT Pub. No.: WO2009/079634
PCT Pub. Date: Jun. 25, 2009

(65) Prior Publication Data
US 2011/0300585 A1    Dec. 8, 2011

Related U.S. Application Data

(60) Provisional application No. 61/014,549, filed on Dec. 18, 2007.

(51) Int. Cl.
*C12P 19/14*    (2006.01)
(52) U.S. Cl. ......................................................... 435/99
(58) Field of Classification Search ........................ None
See application file for complete search history.

(56) References Cited

U.S. PATENT DOCUMENTS

| 4,110,475 A | 8/1978 | Singer |
| 4,657,865 A | 4/1987 | Takasaki |
| 2006/0154352 A1 | 7/2006 | Foody et al. |
| 2007/0062880 A1 | 3/2007 | Ennis |
| 2007/0098825 A1 | 5/2007 | Pierro |
| 2007/0129326 A1 | 6/2007 | Struszczyk et al. |

FOREIGN PATENT DOCUMENTS

JP    10-295390    * 11/1998

OTHER PUBLICATIONS

Li et al., "Amylase partitioning and extractive bioconversion of starch using thermoseparating aqueous two-phase systems", J. Biotechnology, 2002, vol. 93, pp. 15-26.*
Borjesson et al., "Effect of poly(ethylene glycol) on enzymatic hydrolysis and adsorption of cellulase enzymes to pretreated lignocellulose", Enzyme and Microbial Technology, 2007, vol. 41, pp. 186-195.*
Machine Translation of JP 10-295390, Nov. 10, 1998.*
Derwent English Abstract of JP 10-295390, Nov. 10, 1998.*
International Search Report and Written Opinion dated Feb. 24, 2009 for related PCT Patent Application No. PCT/US2008/087472.

* cited by examiner

*Primary Examiner* — Suzanne M Noakes
(74) *Attorney, Agent, or Firm* — Ryan A. Schneider, Esq.; Troutman Sanders LLP

(57) ABSTRACT

The various embodiments of the present invention relate generally to compositions, systems, and methods for altering rates of catalysis. More particularly, the various embodiments of the present invention are directed toward compositions, systems, and methods for enzymatic hydrolysis of polysaccharides, such as cellulose and starch. An aspect of the present invention comprises a method for altering the rate of conversion of a substrate into a product comprising: providing a substrate in a carrier; mixing a reactant and a co-factor with the carrier to form a substantially homogeneous mixture of the reactant, the co-factor, and the substrate in the carrier; and reacting the reactant with the substrate in the presence of the co-factor to convert at least a portion of the substrate into the product, wherein the reaction rate of the reactant with the substrate in the presence of the co-factor is different than the reaction rate of the reactant with the substrate in the absence of the co-factor.

8 Claims, 6 Drawing Sheets

SYSTEMS AND METHODS FOR ALTERING RATES OF ENZYMATIC PROCESSES

RELATED APPLICATIONS

This application, filed under 35 U.S.C. §371, is a U.S. National Stage Application of International Patent Application Serial Number PCT/US2008/087472, filed 18 Dec. 2008, entitled Systems and Methods for Altering Rates of Enzymatic Processes, which claims, under 35 U.S.C. §119 (e), the benefit of U.S. Provisional Application Ser. No. 61/014,549, filed 18 Dec. 2007, the entire contents and substance of which are hereby incorporated by reference as if fully set forth below.

TECHNICAL FIELD

The various embodiments of the present invention relate generally to compositions, systems, and methods for altering rates of catalysis. More particularly, the various embodiments of the present invention are directed toward compositions, systems, and methods for enzymatic hydrolysis of polysaccharides, such as cellulose and starch.

BACKGROUND OF THE INVENTION

Catalysis is a process that increases the rate at which a chemical reaction proceeds. A catalyst is a substance that increases the rate of a chemical reaction, but is not consumed by the chemical reaction. One class of catalysts is enzymes. Similar to other types of catalysts, enzymes speed up reactions by reducing the activation energy for a particular chemical change In enzymatic reactions, enzymes specifically associate with a substrate, and the enzyme catalyzes the chemical conversion of the substrate to a product.

Enzymatic processes are used in wide range of industrial and consumer product applications. As such, the cost of the enzyme is frequently a very significant fraction of the cost of the process or product. Therefore, the capability to increase the efficiency of the enzyme in the enzymatic process product would be very cost-effective. For example, the efficiency of the enzyme could be increased by increasing the rate of the enzymatic process or by reducing the quantity of enzyme needed to achieve a target level of conversion of substrate In one method for the production of biofuels, corn can be milled, and some of the components therein (e.g., starch) can be converted to simple sugars (e.g., glucose) by amylase enzymes. The simple sugars derived from the enzymatic hydrolysis of starch can then be fermented to produce ethanol. In another method for the production of biofuels, cellulosic biomass, such as wood or switchgrass, can be used for the production of ethanol. In such methods, enzymatic conversion of cellulose to simple sugars is performed through the use of enzymes, such as cellulase, and the simple sugars can be fermented to produce ethanol.

In the above methods of enzymatic production of biofuels, the cost of the enzyme is a significant production cost. Thus, compositions, systems, and methods to increase the efficiency of the enzymes, thereby reducing the amount of enzyme needed for such enzymatic processes, would result in significant cost savings, increasing the commercial viability of biofuels generated by enzymatic processes.

Accordingly, there is a need for compositions, systems, and methods to increase the efficiency of the enzymes. It is to the provision of such compositions, systems, and methods to increase the efficiency of the enzymes that the various embodiments of the present invention are directed.

SUMMARY

The various embodiments of the present disclosure relate generally to systems and methods for enhancing rates of catalysis. More particularly, the various embodiments of the present disclosure are directed toward compositions, systems and methods for enzymatic hydrolysis of cellulosic materials and starch-derived materials.

An aspect of the present invention comprises a method for altering the rate of conversion of a substrate into a product comprising: providing a substrate in a carrier; mixing a reactant and a co-factor with the carrier to form a substantially homogeneous mixture of the reactant, the co-factor, and the substrate in the carrier; and reacting the reactant with the substrate in the presence of the co-factor to convert at least a portion of the substrate into the product, wherein the reaction rate of the reactant with the substrate in the presence of the co-factor is different than the reaction rate of the reactant with the substrate in the absence of the co-factor under comparable conditions. In one embodiment of the present invention, the reaction rate of the reactant with the substrate in the presence of the co-factor is greater than the reaction rate of the reactant with the substrate in the absence of the co-factor. In another embodiment of the present invention, the reaction rate of the reactant with the substrate in the presence of the co-factor is less than the reaction rate of the reactant with the substrate in the absence of the co-factor.

In an embodiment of the present invention, the substrate is a macromolecule. In another embodiment of the present invention, the macromolecule is a polysaccharide. The polysaccharide can be cellulose or a derivative thereof, a starch or a derivative thereof, or combinations thereof. In an embodiment of the present invention, the reactant is can be an enzyme. More specifically, the reactant can be cellulase, amylase, or combinations thereof. The reactant can be present in the carrier at a concentration of about 0.001% to about 10%.

In an embodiment of the present invention, the co-factor can be a polymer. In such embodiments, the polymer can be a cationic polymer, or more specifically a cationic polyacrylamide. In an embodiment of the present invention, the polymer can be present in the carrier at concentration less than effective to substantially flocculate the substrate. In an exemplary embodiment of the present invention, the polymer can be present at a concentration less than about 0.1%.

Another aspect of the present invention comprises a method for increasing the rate of hydrolysis of a polysaccharide into glucose comprising: providing a polysaccharide in an aqueous medium; mixing an enzyme and a co-factor with the aqueous medium to form a substantially homogeneous mixture of the enzyme, the co-factor, and the polysaccharide in the aqueous medium; and reacting the enzyme with the polysaccharide in the presence of the co-factor to convert at least a portion of the polysaccharide into glucose, wherein the reaction rate of the enzyme with the polysaccharide in the presence of the co-factor is less than the reaction rate of the enzyme with the polysaccharide in the absence of the co-factor.

The polysaccharide can be cellulose or a derivative thereof, a starch or a derivative thereof, or combinations thereof. The enzyme can be cellulase, amylase, or combinations thereof. The enzyme can be present in the medium at a concentration of about 0.001% to about 10% by volume. In an embodiment of the present invention, the polymer can be a cationic polymer, such as a cationic polyacrylamide. In an embodiment of the present invention, the polymer can be present in the medium at a concentration less than effective to substantially flocculate the polysaccharide. In an embodiment of the present invention, the polymer is present in the aqueous medium at concentration less than effective to flocculate the polysaccharide, such as at a concentration less than about 0.1% by volume. In an embodiment of the present invention, the method can further comprise fermenting the at least a portion of the glucose to produce ethanol.

An aspect of the present invention can comprise a system for polysaccharide catalysis, comprising: a reactor comprising a medium and an agitation element; and the medium comprising a polysaccharide, an enzyme specific for the polysaccharide, and a polymer; wherein the agitation element mixes the medium in the reactor to form a substantially homogenous mixture of the polysaccharide, the enzyme, and the polymer; and wherein the enzyme, in the presence of the polymer, catalyzes the hydrolysis of at least a portion of the polysaccharide to form glucose during a residence time in the reactor.

In an embodiment of the present invention, hydrolysis of at least a portion of the polysaccharide comprises hydrolysis of at least 10% of the polysaccharide. In an embodiment of the present invention, the polysaccharide in the medium comprises a solid phase in and a liquid medium, and wherein the solid phase and liquid medium have the same residence time in the reactor. The polysaccharide can be cellulose or a derivative thereof, a starch or a derivative thereof, or combinations thereof. The enzyme can be cellulase, amylase, or combinations thereof. The enzyme can be present in the carrier at a concentration of about 0.001% to about 10%. In an embodiment of the present invention, the polymer can be a cationic polymer, such as a cationic polyacrylamide. In an embodiment of the present invention, the polymer can be present in the medium at concentration less than effective to substantially flocculate the polysaccharide. In an exemplary embodiment of the present invention, the polymer can be present at a concentration less than about 0.1%. In an embodiment of the present invention, the system can further comprise a fermenter, wherein fermenter is in fluid communication with the reactor, and wherein at least a portion of the glucose produced in the reactor is provided to the fermenter to convert the glucose to ethanol.

An aspect of the present invention can comprise a composition comprising a polysaccharide, a cationic polyacrylamide, and a glycoside hydrolase, wherein the cationic polyacrylamide binds the glycoside hydrolase to the polysaccharide. The polysaccharide can be cellulose or a derivative thereof, a starch or a derivative thereof, or combinations thereof. In an embodiment of the present invention, the glycoside hydrolase can be cellulase, amylase, or a combination thereof. In an embodiment of the present invention, the glycoside hydrolase is present in the medium at a concentration of about 0.001% to about 10%. The cationic polymer can have a molecular weight of about 100,000 Da to about 20 million Da and a cationicity of about 5% to about 95%. In an embodiment of the present invention, the polymer can be present at a concentration less than about 0.1%.

An aspect of the present invention comprises a method for altering the rate of conversion of a substrate into a product comprising: providing a substrate in a carrier; mixing a reactant and a co-factor with the carrier to form a substantially homogeneous mixture of the reactant, the co-factor, and the substrate in the carrier; and reacting the reactant with the substrate in the presence of the co-factor to convert at least a portion of the substrate into the product, wherein the reaction of the reactant with the substrate in the presence of the co-factor proceeds at a higher temperature than the reaction temperature of the reactant with the substrate in the absence of the co-factor. In various embodiments of the present invention, the method can further comprise reducing the thermal degradation of the reactant. In such embodiments, the reaction temperature can be less than about 85° C.

In an embodiment of the present invention, the substrate is a macromolecule. In an embodiment of the present invention, the macromolecule is a polysaccharide. The polysaccharide can be cellulose or a derivative thereof, a starch or a derivative thereof, or combinations thereof. In an embodiment of the present invention, the reactant is can be an enzyme. More specifically, the reactant can be cellulase, amylase, or combinations thereof. The enzyme can be present in the carrier at a concentration of about 0.001% to about 10%.

In an embodiment of the present invention, the co-factor can be a polymer. In such embodiments, the polymer can be a cationic polymer, or more specifically a cationic polyacrylamide. In an embodiment of the present invention, the polymer can be present in the carrier at concentration less than effective to substantially flocculate the substrate. In an exemplary embodiment of the present invention, the polymer can be present at a concentration less than about 0.1%.

Other aspects and features of embodiments of the present invention will become apparent to those of ordinary skill in the art, upon reviewing the following description of specific, exemplary embodiments of the present invention in conjunction with the accompanying figures.

DETAILED DESCRIPTION

Figure 1:
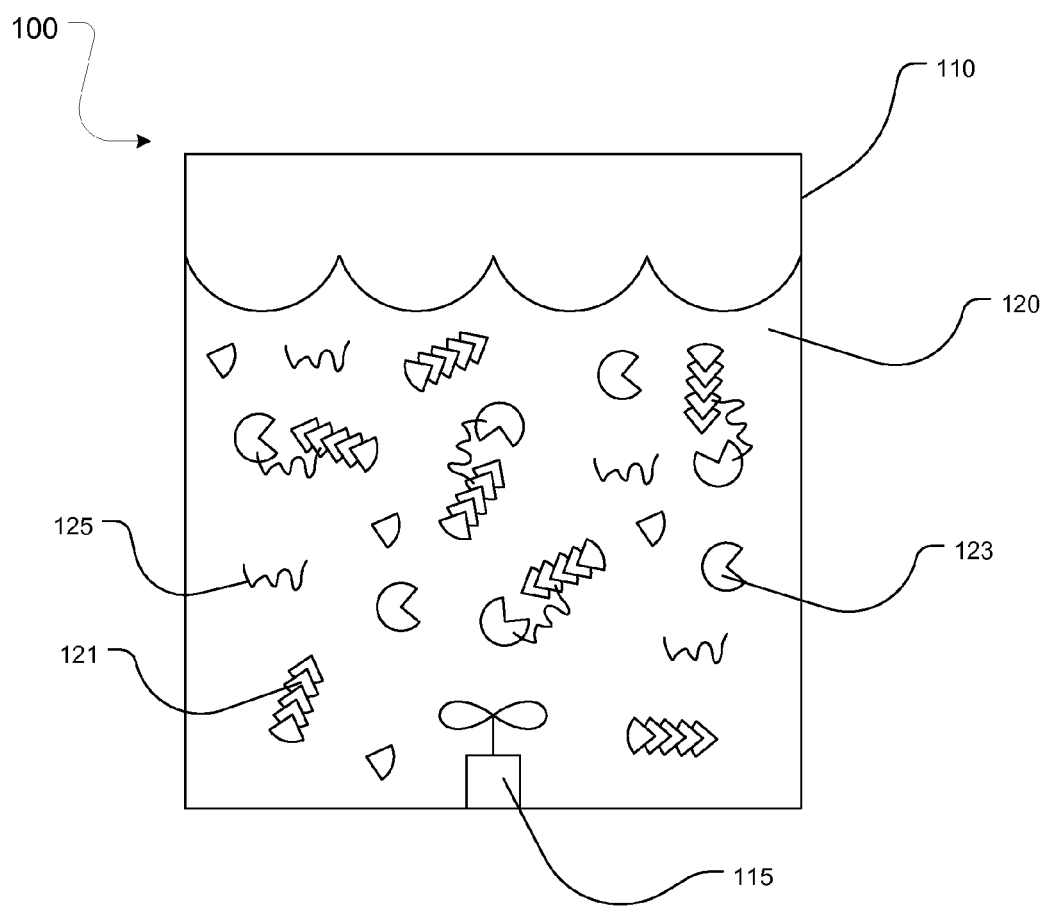
FIG. 1 is a schematic of a system for polysaccharide catalysis

Biofuels comprising ethanol are currently produced from feedstocks, such as corn, sugar cane, and sugar beets. The production of ethanol from these sources, however, cannot be expanded much further, given the limited farmland suitable for the production of such crops and the competing interest of consumption by animals, including humans. Thus, systems and methods to optimize the conversion of these feedstocks to ethanol are needed.

Furthermore, the use of non-food crops, such as cellulosic biomass, for the production of biofuels is gaining interest as a more viable source for the production of biofuels. Cellulosic ethanol production uses non-food crops or inedible waste products, and thus, does not divert food away from the animal/human food chain. In fact, cellulosic biomass often comprises lignocellulose, which is the "woody" structural material of plants. Cellulosic biomass can comprise many cellulosic feedstocks including, but not limited to, agricultural wastes, such as corn stover, wheat straw, barley straw, oat straw, oat hulls, canola straw, and soybean stover; grasses, such as switchgrass, miscanthus, cord grass, and reed canary grass; forestry wastes; and (4) sugar processing residues such as bagasse and beet pulp. As evidenced by these examples, cellulosic feedstocks are both abundant and diverse, and in some cases, pose significant disposal problems. Therefore, systems and methods to facilitate the efficient conversion of cellulose to ethanol are needed.

An aspect of the present invention comprises a method for altering the rate of conversion of a substrate into a product comprising: providing a substrate in a carrier; mixing a reactant and a co-factor with the carrier to form a substantially homogeneous mixture of the reactant, the co-factor, and the substrate in the carrier; and reacting the reactant with the substrate in the presence of the co-factor to convert at least a portion of the substrate into the product, wherein the reaction rate of the reactant with the substrate in the presence of the co-factor is different than the reaction rate of the reactant with the substrate in the absence of the co-factor.

As used herein, the term "substrate" refers to a substance upon which the reactant acts. Various embodiments of the present invention are directed to many substances known in the art, including natural and synthetic substrates as well as organic and inorganic substrates, and various combinations thereof. In an embodiment of the present invention, the substrate is a biological macromolecule, such as a nucleic acid, a protein, a carbohydrate, or a lipid. In an alternative embodiment of the present invention, the substrate can be a nucleotide, an oligonucleotide, an amino acid, a peptide, a sugar or a monosaccharide, an oligosaccharide, an alcohol, a fatty acid. In an exemplary embodiment of the present invention, the substrate is a polysaccharide. A polysaccharide can comprise storage polysaccharides, such as starch and glycogen, or structural polysaccharides, such as lignocellulose, cellulose, chitin, or derivatives thereof. In an embodiment of the present invention, the fiber mass can comprises about 50% to about 1%.

In an exemplary embodiment of the present invention, the polysaccharide can comprise cellulose including, but not limited to cellulose derived from hardwoods, softwoods, or combinations thereof. Suitable hardwoods can include, but are not limited to, Afzelia, Agba yun, Albizia, Alder, Applewood, Ash, Aspen, Ayan, Balsa, Bamboo, Basswood, Beech, Birch, Blackbean, Blackwood, Bocote, Boxelder, Boxwood, Brazilwood, Bubinga, Buckeye, Butternut, Carapa, Catalpa, Cherry, Chestnut, Coachwood, Cocobolo, Corkwood, Cottonwood, Cucumbertree, Dogwood, Ebony, Elm, Eucalyptus, Greenheart, Grenadilla, Gum, Hickory, Hornbeam, Hophornbeam, Ipê, Iroko, Ironwood, Jacarandá, Jatobá, Lacewood, Laurel, Limba, Locust, Mahogany, Maple, Meranti, Mpingo, Oak, Obeche, Okoumé, Oregon Myrtle, Palmwood, Pear, Pernambuco, Poplar, Ramin, Redcedar, Rosewood, Sal, Sandalwood, Sassafras, Satinwood, Silky Oak, Silver Wattle, Snakewood, Sourwood, Spanish-cedar, Sycamore, Teak, Walnut, Willow, and Yellow-poplar, among others. Suitable softwoods can include, but are not limited to, Araucaria, Cedar, Rocky Mountain Douglas-fir, European Yew, Fir, Hemlock, Kauri, Kaya, Larch, Pine, Corsican pine, Jack pine, Lodgepole pine, Monterey pine, Ponderosa pine, Red pine, Scots pine, Red pine, White pine, Sugar pine, Southern Yellow pine, Loblolly pine, Longleaf pine, Pitch pine, Shortleaf pine, Redcedar, Redwood, Rimu, Spruce, Sugi, Whitecedar, and Yellow-cedar, among others. In another embodiment of the present invention, the polysaccharide can comprise a cellulose derivative, such as cellulose esters including, but not limited to, cellulose acetate, cellulose triacetate, and cellulose ethers including, but not limited to, ethylcellulose, methylcellulose, hydroxypropyl cellulose, carboxymethyl cellulose, hydroxypropyl methyl cellulose, and hydroxyethyl methyl cellulose.

In another exemplary embodiment of the present invention, a polysaccharide can comprise a starch including, but not limited to, corn starch, high amylose starch, wheat starch, rice starch, potato starch, arrowroot starch, tapioca starch, sago starch, esterfied derivatives thereof, etherfied derivatives thereof, oxidized derivatives thereof, acid-treated derivatives thereof, dextrinated starch substitute derivatives, and combinations thereof. In an exemplary embodiment of the present invention, the concentration can be less than or equal to about 30%.

The carrier for the substrate can comprise many suitable media known in the art including, but not limited to, a fluid, a liquid, a solid, a solution, a suspension, an emulsion, a gas, a vapor, a gel, a dispersion, a flowable material, a multiphase material, or combination thereof. In an exemplary embodiment of the present invention, the medium can comprise water or a physiologically buffered solution suitable for reacting a reactant with a substrate in the presence of a co-factor.

As used herein, the term "reactant" refers to a substance that acts upon the substrate to chemically convert the substrate into a product. In an embodiment of the present invention, a reactant is a catalyst. Various embodiments of the present invention contemplate the use of many catalysts known in the art. In an exemplary embodiment of the present invention, the catalyst is an enzyme. An enzyme can be an oxidoreductase, a transferase, a hydrolase, a lysase, an isomerase, a ligase, or a combination thereof. In an exemplary embodiment of the present invention, the enzyme comprises a hydrolase. A hydrolase can comprise an esterase (e.g., a lipase, phospholipase), a protease, or a glycoside hydrolase, among others.

In an exemplary embodiment of the present invention, an enzyme can comprise a cellulase, a hemicellulase, a lignocellulase, or combinations thereof. As used herein, the term "cellulase" comprises an enzyme with at least some specificity for cellulose including, but not limited to an endocellulase, an exocellulase, a cellobiase (e.g., beta-glucosidase), an oxidative cellulase (e.g., cellobiose dehydrogenase), or a cellulose phosphorylase. A cellulase can comprise an enzyme capable of converting cellulose to glucose, cellbiose, cell-oligosacchraides, or combinations thereof. A cellulase can hydrolyze $\beta(1\rightarrow4)$glycosidic bonds. For example, a commercial "cellulase" is a mixture of enzymes having at least some specificity for cellulose.

In another exemplary embodiment of the present invention, an enzyme can comprise an amylase. As used herein, the term "amylase" comprises an enzyme with at least some specificity for a starch, including but not limited to an alpha-amylase, a beta-amylase, a gamma-amylase, or a combination thereof. An amylase can comprise an enzyme capable of converting starch to glucose or oligosacchraides. An amylase can hydrolyze $\alpha(1\rightarrow4)$glycosidic bonds.

One of ordinary skill in the art would appreciate that the amount of enzyme required to convert a substrate into a product can vary based on a number of factors, such as the amount of substrate and the reaction conditions (e.g., the reaction temperature, pH), among others. In an embodiment of the present invention, the enzyme is present in the carrier at a concentration of about 0.001% to about 10% (wt/vol). In another embodiment of the present invention, the enzyme is present in the carrier at a concentration of about 0.01% to about 1% (wt/vol). In an embodiment of the present invention, the enzyme is present in the carrier at a concentration of at least about 0.005%. In another embodiment, the enzyme is present in the carrier at a concentration of at least about 0.01%. In an exemplary embodiment of the present invention, the enzyme is present in the carrier at a concentration of about 0.1%. In another exemplary embodiment of the present invention, the enzyme is present in the carrier at a concentration of about 1%.

An aspect of the present invention comprises a method for altering the rate of conversion of a substrate into a product by reacting the reactant with the substrate in the presence of a co-factor to convert at least a portion of the substrate into the product. As used herein, a "co-factor" is a substance that alters the efficiency of conversion of a substrate into a product by the reactant. The co-factor can comprise many substances capable of altering a reaction rate, including but not limited to a nucleic acid, an oligonucleotide, a polynucleotide, an amino acid, a peptide, a protein, an antibody, a sugar, a carbohydrate, a monomer, a polymer, a small molecule, a vitamin, an ion, a co-enzyme, or combinations thereof.

In an exemplary embodiment of the present invention, the co-factor is a polymer. Suitable polymers can be a polyamide, a polyacrylamide, a polyester, a polycarbonate, a hydroxypropylmethylcellulose, polyvinylchloride, polymethacrylate, polystyrene and copolymers thereof, polyvinyl alcohol, polyacrylic acid, polyethylene oxide, and combinations thereof, among others. The polymers used in the compositions, systems, and methods of the present invention can be cationic, anionic, non-ionic, amphoteric, or combinations thereof. Furthermore, the polymers used in the compositions, systems, and methods of the present invention can have various molecular weights and various charge densities. For example, in embodiments of the present invention where the co-factor is a polyacrylamide, the molecular weight of the polyacrylamide can range from about 100,000 Da to about 20 million Da and the charge density can range from about 5% to about 95%. In another embodiment of the present invention, the molecular weight of the polyacrylamide can range from about 1 million Da to about 10 million Da. In an exemplary embodiment of the present invention, the cationic polyacrylamide can have a molecular weight of about 3 million Da to about 10 million Da and a cationicity of about 30% to about 35%.

In an embodiment of the present invention, the polymer is a cationic polymer. In another embodiment of the present invention, the cationic polymer comprises monomers having an amine or imine group. In an exemplary embodiment of the present invention, the cationic polymer is cationic polyacrylamide. In an exemplary embodiment of the present invention, the molecular weight of the polyacrylamide can range from about 100,000 Da to about 20 million Da. In another exemplary embodiment of the present invention, the polyacrylamide can have a cationicity that can range from about 5% to about 95%. In another embodiment of the present invention, the molecular weight of the polyacrylamide can range from about 1 million Da to about 10 million Da. In an exemplary embodiment of the present invention, the cationic polyacrylamide can have a molecular weight of about 3 million Da to about 10 million Da. In an exemplary embodiment of the present invention, the cationic polyacrylamide can have a cationicity of about 30% to about 35%.

The amount of co-factor required to alter the efficiency of conversion of a substrate into a product by the reactant can vary depending upon several variables of the reaction including, but not limited to, the amount of substrate, the amount of enzyme, and the reaction conditions (e.g., temperature, pH), among others. In an embodiment of the present invention, the polymer is present at a concentration in the carrier less than effective to substantially flocculate the substrate under the reaction conditions. As used herein, the phrase "less than effective to substantially flocculate the substrate" refers to concentrations insufficient to induce significant floc formation. For example, in the context of cellulosic biomass in an aqueous medium, the concentration of the polymer is less than effective to significantly aggregate the biomass into a floc.

In an embodiment of the present invention, the polymer is present at a concentration less than about 1% (wt/vol) of the carrier. In another embodiment of the present invention, the polymer is present at a concentration less than about 0.2% (wt/vol) of the carrier. In another embodiment of the present invention, the polymer is present at a concentration less than about 0.1% (wt/vol) of the carrier. In yet another embodiment of the present invention, the polymer is present at a concentration less than about 0.01% (wt/vol) of the carrier. In yet another exemplary embodiment, the polymer is present at a concentration of at least about 0.005%. In another exemplary embodiment, the polymer is present at a concentration of at least about 0.001%. In still another exemplary embodiment of the present invention, the polymer is present at a concentration of at least about 0.0005% (wt/vol) of the carrier. In an exemplary embodiment of the present invention, the polymer is present at a concentration ranging from about 0.01% to about 0.001% (wt/vol) of the carrier.

An aspect of the present invention comprises mixing the substrate, the reactant and the co-factor with the carrier to form a substantially homogeneous mixture of the reactant, the co-factor, and the substrate in the carrier. A "substantially homogeneous mixture" is a mixture where there is a substantially uniform distribution of the components in the mixture. A substantially homogeneous mixture can be in the form of a solution, dispersion, suspension or the like, provided it has a substantially uniform blend of components. In the context of a mixture of solids in a liquid carrier, a substantially homogeneous mixture comprises a substantially uniform distribution of the solids in the liquid. For example, in the context of a cellulosic feedstock in an aqueous medium, a substantially homogeneous mixture comprises a substantially uniform distribution of cellulosic solids in the aqueous medium. Therefore, a cellulosic feedstock in the form of a substantially homogeneous mixture does not comprise a cellulosic solid phase that is substantially distinct from the rest of the mixture. For example, there would be relatively no significant difference in the residence time of solids and liquids of a substantially homogeneous cellulosic-based suspension in a continuous reactor, e.g., a continuous stirred tank reactor.

In an embodiment of the present invention, a method for altering the rate of conversion of a substrate into a product by reacting a reactant with a substrate in the presence of a co-factor can comprise increasing or decreasing the reaction rate of the reactant with substrate for a given residence time. The rate of the reaction can be adjusted based upon the composition and concentration of the co-factor. For example, a method for increasing the rate of conversion of a substrate into a product by reacting the reactant with the substrate in the presence of a co-factor can comprise providing a co-factor comprising cationic polyacrylamide. In another example, a method for decreasing the rate of conversion of a substrate into a product by reacting the reactant with the substrate in the presence of a co-factor can comprise providing a co-factor comprising a cross-linked, cationic polyacrylamide. Various embodiment of the present invention contemplate altering the reaction rate by varying the molecular weight and charge density of the polymer.

Aspects of the methods of the present invention comprise converting at least a portion of the substrate into a product. The conversion of the substrate into a product can comprise a catabolic reaction or an anabolic reaction. Thus, in one embodiment of the present invention, the conversion of at least a portion of the substrate into a product comprises the catalysis of the substrate to generate a product. In an alternative embodiment of the present invention, the conversion of at least a portion of the substrate into a product comprises the synthesis of the substrate to form a product.

In an exemplary embodiment of the present invention, a method for increasing the rate of hydrolysis of a polysaccharide into glucose comprises: providing a polysaccharide in an aqueous medium; mixing an enzyme and a polymer with the aqueous medium to form a substantially homogeneous mixture of the enzyme, the polymer, and the polysaccharide in the aqueous medium; and reacting the enzyme with the polysaccharide in the presence of the polymer to convert at least a portion of the polysaccharide into glucose, wherein the reaction rate of the enzyme with the polysaccharide in the presence of the polymer is greater than the reaction rate of the enzyme with the polysaccharide in the absence of the polymer. In an exemplary embodiment, it should be appreciated that the rate and/or conversion of the polysaccharide into glucose can be altered for a given residence time in the reactor by the addition of the polymer to the reaction system compared to a system without the polymer.

More specifically, the polysaccharide substrate can be cellulose or a derivative thereof, or starch or a derivative thereof. Such methods can further comprise fermenting at least a portion of the glucose to produce ethanol.

Another aspect of the present invention comprises a method for altering the rate of conversion of a substrate into a product, wherein the reaction of the reactant with the substrate in the presence of the co-factor proceeds at a higher temperature than the reaction temperature of the reactant with the substrate in the absence of the co-factor. In an embodiment of the present invention, the co-factor thermally stabilizes the reactant. In an exemplary embodiment of the present invention, a cationic polymer stabilizes the enzyme. In an embodiment of the present invention, the reaction of a reactant with a substrate in the presence of a co-factor can be performed at a temperature less than about 85° C. In another embodiment of the present invention, the reaction of a reactant with a substrate in the presence of a co-factor can be performed at a temperature less than about 60° C.

The various embodiments of the present invention also contemplate systems for substrate catalysis. A system for substrate catalysis can comprise a reactor comprising a carrier and an agitation element; and the carrier comprising a substrate, a reactant, and a co-factor; wherein the agitation element mixes the carrier in the reactor to form a substantially homogenous mixture of the substrate, the reactant, and the co-factor in the carrier; and wherein the reactant, in the presence of the co-factor, catalyzes the catalysis of at least a portion of the substrate to form a product during a residence time in the reactor.

Referring now to the figures, wherein like reference numerals represent like parts throughout the several views, exemplary embodiments of the present invention will be described in detail. Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. As shown in FIG. 1, an aspect of the present invention comprises a system 100 for polysaccharide catalysis, comprising: a reactor 110 comprising a carrier 120 and an agitation element 115; and the carrier 120 comprising a polysaccharide 121, an enzyme 123 specific for the polysaccharide 121, and a polymer 125; wherein the agitation element 115 mixes the carrier 120 in the reactor 110 to form a substantially homogenous mixture of the polysaccharide 121, the enzyme 123, and the polymer 125 in the carrier 120; and wherein the enzyme 123, in the presence of the polymer 125, catalyzes the hydrolysis of at least a portion of the polysaccharide 121 to form glucose during a residence time in the reactor 110.

In various embodiments of systems 100 for polysaccharide catalysis, a reactor 110 can comprise many non-upflow, non-settling reactors known in the art. In an exemplary embodiment of the present invention, a reactor 110 can comprise a batch reactor. The reactor 110 can also comprise a substantially mixed continuous reactor or a sequence of batch continuous reactors known in the art. The systems 100 of the present invention can be used for the catalysis of many biological macromolecules, such as polysaccharides 123 including, but not limited to, cellulose and starch.

The enzyme 123 used in the system 100 for polysaccharide catalysis depends largely upon the polysaccharide to be catalyzed. In an exemplary embodiment of a system 100 for polysaccharide catalysis, an enzyme 123 can comprise a cellulase, a hemicellulase, a lignocellulase, or combinations thereof. In another exemplary embodiment of a system 100 for polysaccharide catalysis, an enzyme 123 can comprise an amylase.

The amount of enzyme required to hyrdolyze at least a portion of a polysaccharide into glucose can vary depending on several conditions of the reaction. In an embodiment of the present invention, the enzyme 123 is present in the carrier 120 can vary form a concentration of about 0.001% to about 10% (wt/vol). In an exemplary embodiment of the present invention, the enzyme 123 is present in the carrier 120 at a concentration of about 1%. In another exemplary embodiment of the present invention, the enzyme 123 is present in the carrier 120 at a concentration of about 0.1%. In another exemplary embodiment of the present invention, the enzyme 123 is present in the carrier 120 at a concentration of about 0.03%. In another embodiment, the enzyme 123 is present in the carrier 120 at a concentration of at least about 0.01%. In yet another exemplary embodiment of the present invention, the enzyme 123 is present in the carrier 120 at a concentration of at least about 0.005%. %.

The polymer 125 used in the system 100 of the present invention can be cationic, anionic, non-ionic, amphoteric, or combinations thereof. In an embodiment of the present invention, the polymer 125 is a cationic polymer. In another embodiment of the present invention, the cationic polymer comprises monomers having an amine or imine group. In an exemplary embodiment of the present invention, the cationic polymer is cationic polyacrylamide. In an exemplary embodiment of the present invention, the molecular weight of the cationic polyacrylamide can range from about 100,000 Da to about 20 million Da. In another exemplary embodiment of the present invention, the cationic polyacrylamide can have a cationicity that can range from about 5% to about 95%. In an exemplary embodiment of the present invention, the cationic polyacrylamide can have a molecular weight of about 3 million Da to about 10 million Da and a cationicity of about 30% to about 35%. In an embodiment of the present invention, the polymer 125 is present at a concentration in the carrier 120 less than effective to substantially flocculate the substrate 121. In an exemplary embodiment of the present invention, the polymer 125 is present at a concentration less than about 0.2% (wt/vol) of the carrier 120. In another embodiment of the present invention, the polymer 125 is present at a concentration less than about 0.1% (wt/vol) of the carrier 120. In yet another embodiment of the present invention, the polymer 125 is present at a concentration less than about 0.01% (wt/vol) of the carrier 120. In an exemplary embodiment of the present invention, the polymer 125 is present at a concentration ranging from about 0.01% to about 0.001% (wt/vol) of the carrier 120. In another exemplary embodiment, the polymer 125 is present at a concentration of at least about 0.005% of the carrier 120. In yet another exemplary embodiment, the polymer 125 is present at a concentration of at least about 0.0005% (wt/vol) of the carrier 120. In another exemplary embodiment of the present invention, the polymer 125 is present at a concentration of at least about 0.001 of the carrier 120.

An aspect of a system 100 for polysaccharide catalysis comprises an agitation element 115. The agitation element 115 mixes the enzyme 123, the polysaccharide 121, and the polymer 125 in the carrier 120 to form a substantially homogeneous mixture of the enzyme 123, the polymer 125, and the polysaccharide 121 in the carrier 120. The agitation element 115 can comprise many devices known in the art capable of mixing a carrier including, but not limited to, an impeller, a blade, a fan, a fin, an oar, a paddle, a screw, a high shear mixer, a homogenizer, a stirring element, a shaking element, an element capable of inverting the reactor, or the like.

For example, in the context of providing a cellulosic feedstock in an aqueous medium to a reactor, an agitation element mixes the carrier comprising an enzyme, the cellulosic biomass, and the polymer to create a substantially homogeneous mixture comprising a substantially uniform distribution of cellulosic solids in the aqueous medium within the reactor. Therefore, a substantially homogeneous mixture does not comprise a solid phase or floc that is wholly or partially separated from the remaining mixture. As such, there would be relatively no difference in the residence time of solids and liquids of a substantially homogeneous cellulosic-based solution in a reactor.

In an embodiment of a system 100 for polysaccharide catalysis, at least a portion of the polysaccharide is hydrolyzed by the enzyme to produce glucose. In one embodiment of the present invention, at least about 10% of the polysaccharide is hydrolyzed to produce glucose. In another embodiment of the present invention, at least about 25% of the polysaccharide is hydrolyzed to produce glucose. In another embodiment of the present invention, at least about 50% of the polysaccharide is hydrolyzed to produce glucose. In another embodiment of the present invention, at least about 80% of the polysaccharide is hydrolyzed to produce glucose. In another embodiment of the present invention, at least about 90% of the polysaccharide is hydrolyzed to produce glucose. In another embodiment of the present invention, at least about 95% of the polysaccharide is hydrolyzed to produce glucose. In another embodiment of the present invention, at least about 98% of the polysaccharide is hydrolyzed to produce glucose. In another embodiment of the present invention, at least about 99% of the polysaccharide is hydrolyzed to produce glucose.

In yet another embodiment of the present invention, a system 100 for polysaccharide catalysis, comprises mixing and reacting a polysaccharide 121, an enzyme 123 specific for the polysaccharide, and a polymer 125 in a reactor 110 promote enzymatic hydrolysis of the polysaccharide 121, wherein hydrolysis of the polysaccharide is determined by reduction of average fiber length. Thus, various embodiments of the systems and methods of the present invention are directed toward the reduction of the average fiber length in cellulosic biomass. In one embodiment of the present invention, the average fiber length in feedstock is reduced by at least about 10%. In another embodiment of the present invention, the average fiber length in feedstock is reduced by at least about 25%. In another embodiment of the present invention, the average fiber length in feedstock is reduced by at least about 50%. In another embodiment of the present invention, the average fiber length in feedstock is reduced by at least about 80%. In another embodiment of the present invention, the average fiber length in feedstock is reduced by at least about 95%. In another embodiment of the present invention, the average fiber length in feedstock is reduced by at least about 98%. In another embodiment of the present invention, the average fiber length in feedstock is reduced by at least about 99%.

The systems and methods of the present inventions can operated or performed under various reaction conditions suitable to enable catalytic activity of the enzyme. For example, a system for polysaccharide catalysis can be operated at temperatures below about 60° C. In an exemplary embodiment of the present invention, a system for polysaccharide catalysis can be operated at a temperature of about 50° C. to about 52° C. Systems and methods for polysaccharide catalysis can be operated for durations of time ranging from about 0.5 hours to about 10 days. Thus, feedstock can have a residence time in the reactor ranging from about 0.5 hours to about 10 days.

In an embodiment of the present invention, a system 100 for polysaccharide catalysis can further comprise a fermenter 130, wherein fermenter 130 is in fluid communication with the reactor 110, and wherein at least a portion of the glucose produced in the reactor 110 is provided to the fermenter 130 to convert the glucose to ethanol. In one embodiment of the present invention, the reactor 110 and the fermenter 130 are distinct structures. In an alternative embodiment of the present invention, the reactor and the fermenter are the same structures. An aspect of the present invention comprises a composition comprising a substrate, a reactant, and a co-factor, wherein the co-factor tethers or binds the enzyme to the substrate. In an embodiment of the present invention, a composition comprises a substrate, a polymer, and an enzyme, wherein the polymer tethers or binds the enzyme to the substrate. In an exemplary embodiment of the present invention, a composition comprises a polysaccharide, cationic polyacrylamide, and a glycoside hydrolase, wherein the cationic polyacrylamide tethers or binds the glycoside hydrolase to the polysaccharide. In such embodiments, the polysaccharide can comprise cellulose, starch, or combinations thereof, and the glycoside hydrolase can comprise a cellulase, a hemicellulase, a lignocellulase, an amylase, or combinations thereof. In such embodiments, the cationic polyacrylamide can have a molecular weight of about 100,000 Da to about 20 million Da and a cationicity of about 5% to about 95%. In an exemplary embodiment of the present invention, the cationic polyacrylamide can have a molecular weight of about 3 million Da to about 10 million Da and a cationicity of about 30% to about 35%.

In an embodiment of the present invention, the glycoside hydrolase is present in the composition at a concentration of about 0.001% to about 10% (wt/vol). In an exemplary embodiment of the present invention, the enzyme is present in the composition at a concentration of about 1%. In another exemplary embodiment of the present invention, the enzyme is present in the composition at a concentration of about 0.1%.

In an embodiment of the present invention, the polymer is present at a concentration in the composition less than effective to substantially flocculate the composition. In an exemplary embodiment of the present invention, the polymer is present at a concentration less than about 0.2% (wt/vol) of the composition. In another embodiment of the present invention, the polymer is present at a concentration less than about 0.1% (wt/vol) of the composition. In yet another embodiment of the present invention, the polymer is present at a concentration less than about 0.1% (wt/vol) of the composition. In an exemplary embodiment of the present invention, the polymer is present at a concentration ranging from about 0.01% to about 0.001% (wt/vol) of the composition.

Various embodiments of the present invention can comprise systems and methods for the conversion of cellulose to sludge. For example, cellulase can degrade cellulose to dissolved materials (e.g., glucose, cellobiose (collectively, the biochemical oxygen demand ("BOD")). The BOD can then be converted to methane. Thus, systems and methods for the conversion of sludge to BOD can be coupled with systems and methods for the conversion of BOD to methane.

It must be noted that, as used in this specification and the appended claims, the singular forms "a," "an," and "the" include plural referents unless the context clearly dictates otherwise. In addition, all patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure. Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Therefore, while embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

EXAMPLES

Example 1

Hydrolysis of Pulp Fiber in the Presence of a Cationic Polymer

Figure 2:
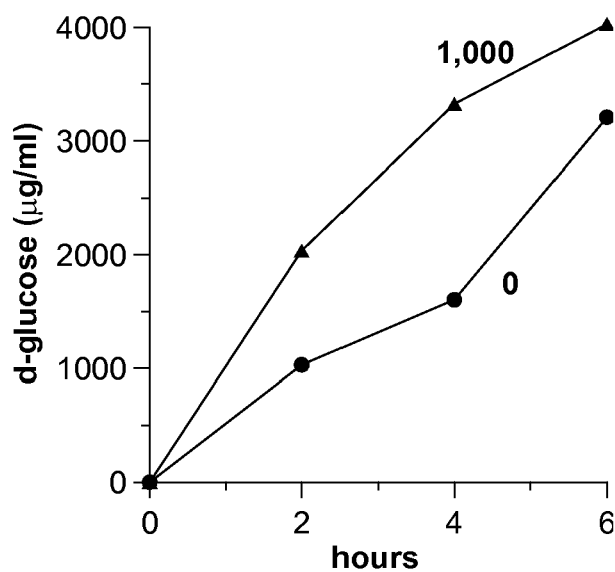
FIG. 2 illustrates the effect of a linear c-PAM on the efficiency of a cellulase enzyme.
Figure 3:
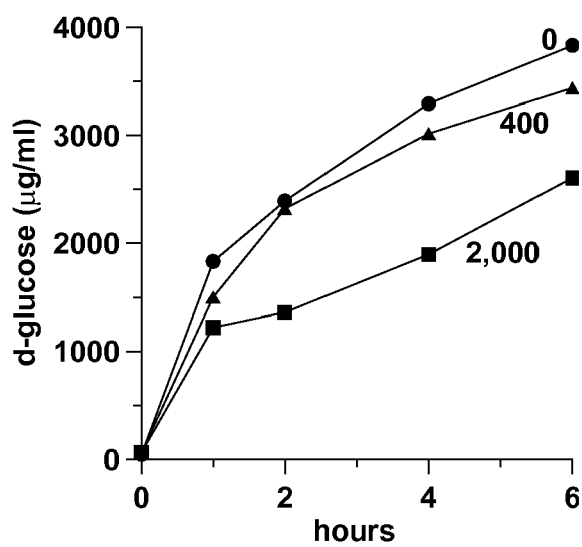
FIG. 3 demonstrates the effect of a cross-linked c-PAM on the efficiency of a cellulase enzyme.

In the present example, bleached kraft pulp fiber in a well-mixed 1% suspension by weight in water (pH=4.7) is hydrolyzed by a cellulase enzyme of a known type present at 1% concentration. The enzyme was a product from Novozymes Inc. and was identified as Pergalase. The generation of glucose from the enzymatic degradation of the pulp is illustrated in FIG. 2. The values for c-PAM in FIG. 2 are shown in ppm of water. When a similar degradation is conducted in the presence of a known type of linear cationic polyacrylamide (c-PAM) polymer (35% SH, Eka Chemicals) and provided at a concentration of 1,000 ppm, the rate of glucose production increased beyond the level achieved by the enzyme alone as shown in FIG. 2. This increase in rate is very beneficial inasmuch that it enables a more efficient use of the enzyme. The reaction rate acceleration, however, is not obtained for all c-PAMs. A cross-linked c-PAM (AF4380, Axchem Inc.) retards the rate of glucose generation from fiber as shown in FIG. 3. The values for c-PAM in FIG. 3 are shown in ppm. Such retardation may be useful in situations where the activity of an enzyme needs to be curtailed at a given stage in a process.

Figure 4:
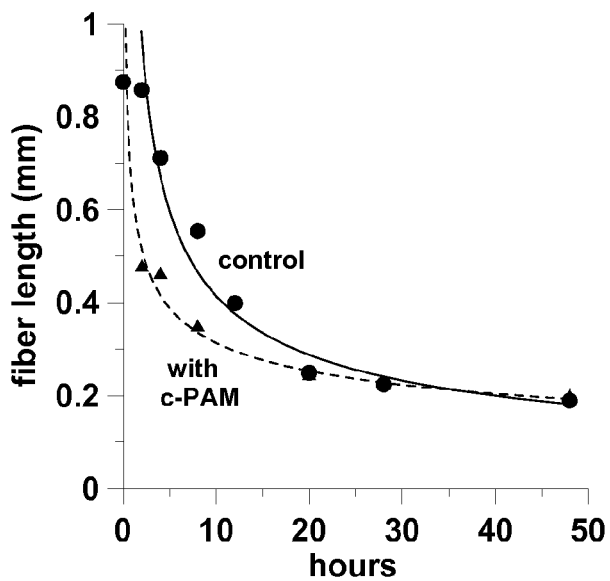
FIG. 4 shows the effect of 4800 SSH c-PAM on the degradation of bleached hardwood fiber.

An illustration of the beneficial effect of c-PAM is provided in FIG. 4 where the average fiber length of a suspension of bleached hardwood fibers, present as a well-mixed 1% suspension in water (pH=4.7), was monitored by a commercially available device, the Fiber Quality Analyzer (Optest Equipment Inc.). The measurements were made in the presence of 1% Pergalase. A parallel measurement was made with a commercially available c-PAM (4800 SSH from SNF Inc.), which was added to the suspension at 100 ppm. The c-PAM significantly accelerates the rate of reduction of the fiber length caused by the enzyme, as indicated in FIG. 4.

Figure 5:
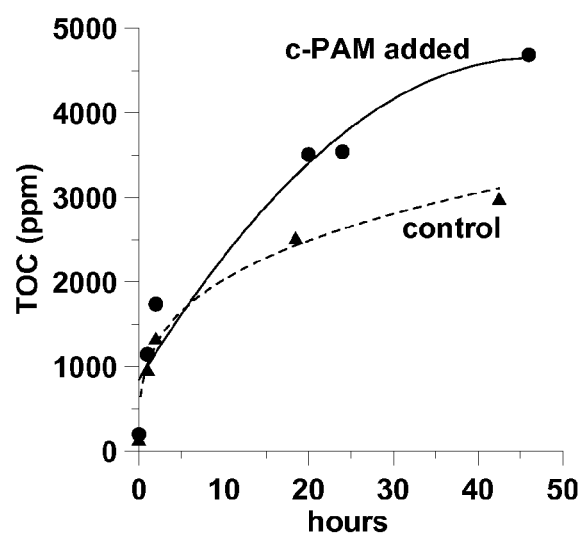
FIG. 5 illustrates the effect of PL2320 c-PAM on the degradation of bleached hardwood fiber.

As illustrated in FIG. 5, bleached hardwood fiber is mixed with a cellulose preparation having a concentration of about 0.1% (wt/vol) in water (pH=4.7) at 47° C. The fiber dissolves and soluble organic material is generated. The Total Organic Carbon (TOC) of the dissolved organic material can be measured by TOC analyzers, which are well known in the art. The TOC values represent the concentration of carbon atoms in the dissolved organic molecules generated from the disintegration of the fiber. The curve designated as "control" in FIG. 5 represents cellulosic fiber degraded by the enzyme alone. The "c-PAM added" curve was obtained when 1,000 ppm of a commercial c-PAM formulation was added to the mixture of fiber and enzyme described for the "control" experiment one hour after initiation of the reaction.

The c-PAM formulation was identified as PL2320 and was obtained from Eka Chemicals. This formulation contained about 38% of the c-PAM as active ingredient. Based on the data presented in FIG. 5, the presence of the c-PAM greatly accelerates the rate of degradation of the fiber to dissolved organic material.

Figure 6:
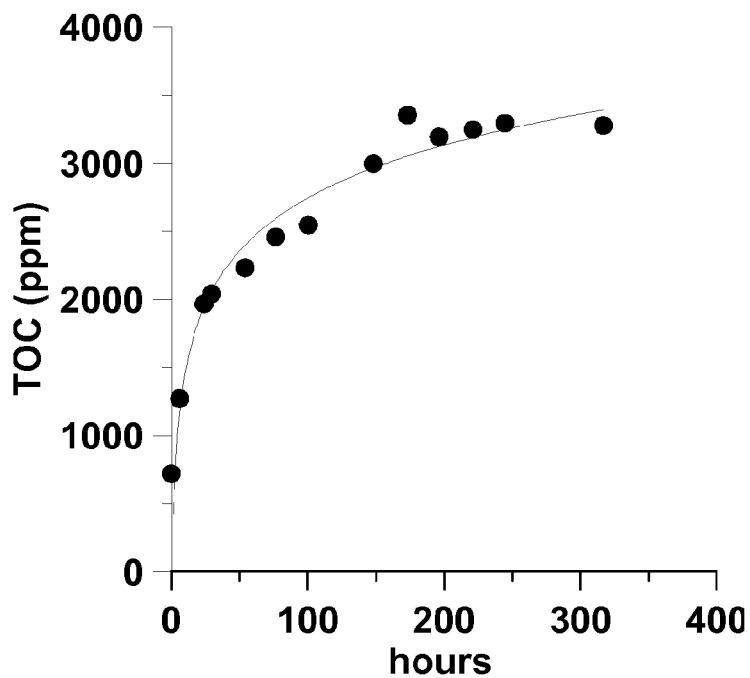
FIG. 6 demonstrates the effect of PL2320 c-PAM on the degradation of bleached hardwood fiber with an enzyme concentration of 0.03%.

Results from an experiment with a lower enzyme concentration of 0.03% are shown in FIG. 6. The mixture comprised a suspension of 3.5% bleached hardwood fiber in water (pH=4.7) at 47° C. The polymer, c-PAM (PL2320), was present at 740 ppm, and the suspension was well-mixed throughout the experiment. Based on the data presented in FIG. 6, the fiber is degraded as indicated by the rise in TOC.

Example 2

Hydrolysis of Starch in the Presence of a Cationic Polymer

Figure 7:
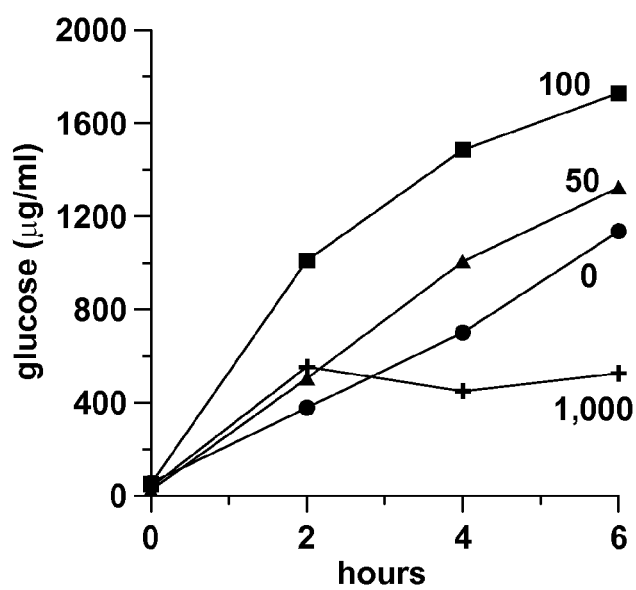
FIG. 7 demonstrates the effect of a c-PAM (35% SH) on the efficiency of an amylase enzyme.

The systems and methods of the present invention are also applicable to soluble substrates, such as unmodified grain starches, like corn starch, high amylose starch, wheat starch, and rice starch, potato starches such as potato starch and tapioca starch, and esterified, etherified, oxidized, acid treated, or dextrinated starch-substituted derivatives of these starches, among others. In the present example, 1% corn starch in water was reacted with a commercially available amylase enzyme preparation (Buzyme 2506, Buckman Laboratories) present at a 1% concentration. The rate of conversion of starch to glucose is accelerated in the presence of c-PAM (35% SH) with increasing c-PAM concentration up to 100 ppm, as illustrated in FIG. 7. A higher polymer of 1,000 ppm reduces the amount of glucose produced. Hence, the efficiency of the enzyme can be regulated by either increasing or decreasing the polymer dose.

Figure 8:
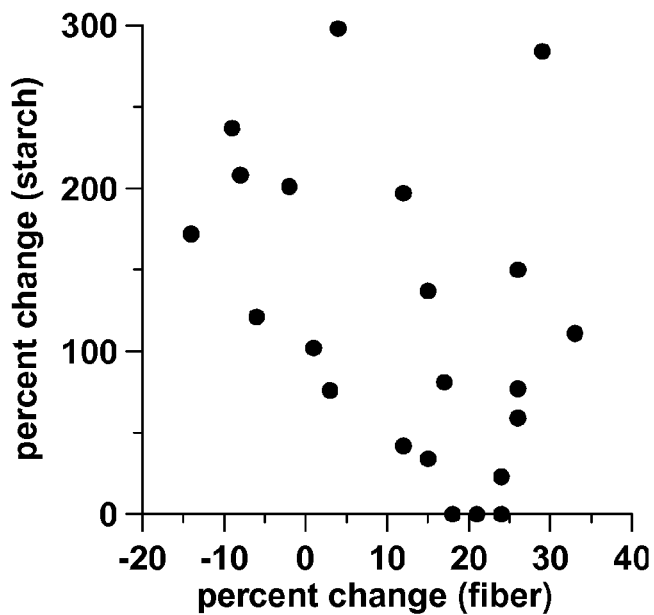
FIG. 8 shows the effect of various c-PAMs on the efficiency of amylase on cornstarch (ordinate) and on cellulase on fiber (abscissa).

Several members of the c-PAM family are effective in catalyzing both the cornstarch and fiber applications albeit to varying degrees. Screening measurements were made with twenty-two commercial c-PAM formulations varying in charge, molecular weight, and the degree of branching. Aqueous suspensions of bleached softwood fiber or cornstarch (1%) were shaken with 1% of cellulase or amylase, respectively. Polymer was added at 100 ppm for cornstarch and at 500 ppm for the cellulose fiber at the beginning of the process. Changes in the amount of glucose generated in the presence of the polymers measured from duplicate experiments are illustrated in FIG. 8. Except for three instances where there was no effect, the c-PAMs provide a benefit for the cornstarch application. For the fiber work, five of the polymers tested were inhibitory; they have negative values on the abscissa, which include linear and branched polymers having a cationicity of 5% to about 80%. Although the cationicity of these polymers appears appropriate, the structure of the polymer may play a role in the ability of the polymer to enhance the reaction rate. This example further demonstrates that the same c-PAM can enhance the effect of two different enzymes on two different substrates, one macromolecular and the other solid, demonstrating that a wide range of polymers can be effective.

Example 3

Binding of Substrate to Enzyme by a Cationic Polymer

In order to demonstrate that c-PAM enhances the binding of cellulase enzyme to fiber, handsheets were exposed to the enzyme with and without the presence of c-PAM, and the degree of binding of the enzyme to the handsheet compared. Handsheets were used in place of a fiber suspension to remove the possibility of floc formation as the fibers were already formed into a sheet. A sample of softwood bleached kraft pulp was suspended in water and screened with a #28 mesh screen to remove fines and short fibers as described in TAPPI test Method T233 (TAPPI Press, Atlanta, Ga.). The fiber sample was then made into handsheets as described in TAPPI Test Method T-205. One set of handsheets was treated with a solution of a c-PAM (35% SH, Eka Chemicals prepared at 200 ppm) in water for 30 minutes in order to allow the c-PAM to be taken up by the fibers in the handsheet. An equivalent set of handsheets was exposed to a comparable volume of plain water for the same period of time.

Figure 9:
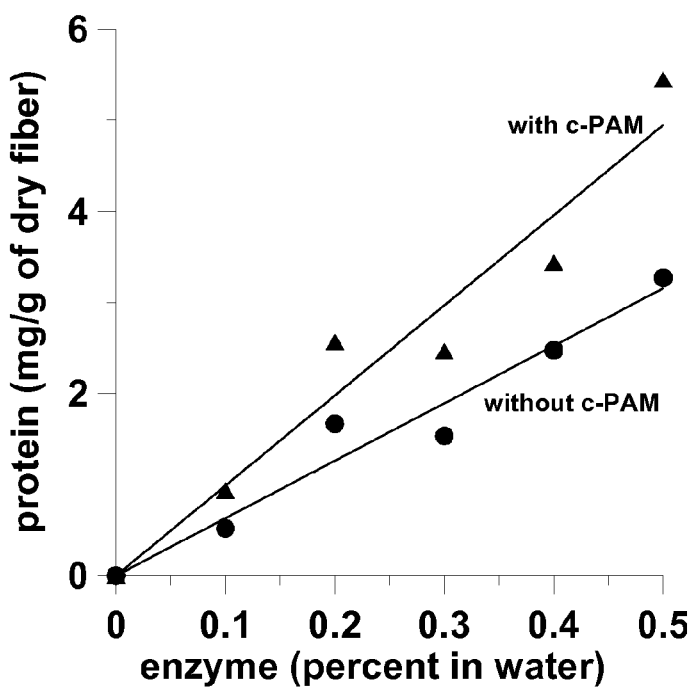
FIG. 9 illustrates the effect of c-PAM on enzyme binding to substrate.

Both sets of handsheets were dried at room temperature and then soaked in 0.1%, 0.2%, 0.3%, 0.4%, and 0.5% aqueous solutions of Pergalase at 4° C. for 20 minutes. The enzyme remaining in the supernatant was assayed with a Protein Assay kit obtained Thermo Scientific. The amount of enzyme bound to the fiber was then obtained by taking the difference between the amount of enzyme initially added and that remaining in solution after exposure to the handsheet. The results embodied in FIG. 9 show that the c-PAM treated handsheets picked up more enzyme demonstrating that the presence of c-PAM enhanced the binding of enzyme to fiber across various enzyme concentrations.

While not meaning to limit the scope and applicability of the invention in any way, it is believed that the rate acceleration occurs when the polymer loosely binds the enzyme to the substrate, effectively tethering the enzyme to the substrate and thereby increasing the probability of beneficial contact between sites in the enzyme and sites in the substrate. It is believed that the rate deceleration occurs when the binding is of a type that decreases the probability of said contact.

Example 4

Stabilization of Enzyme by a Cationic Polymer at Elevated Temperatures

Figure 10:
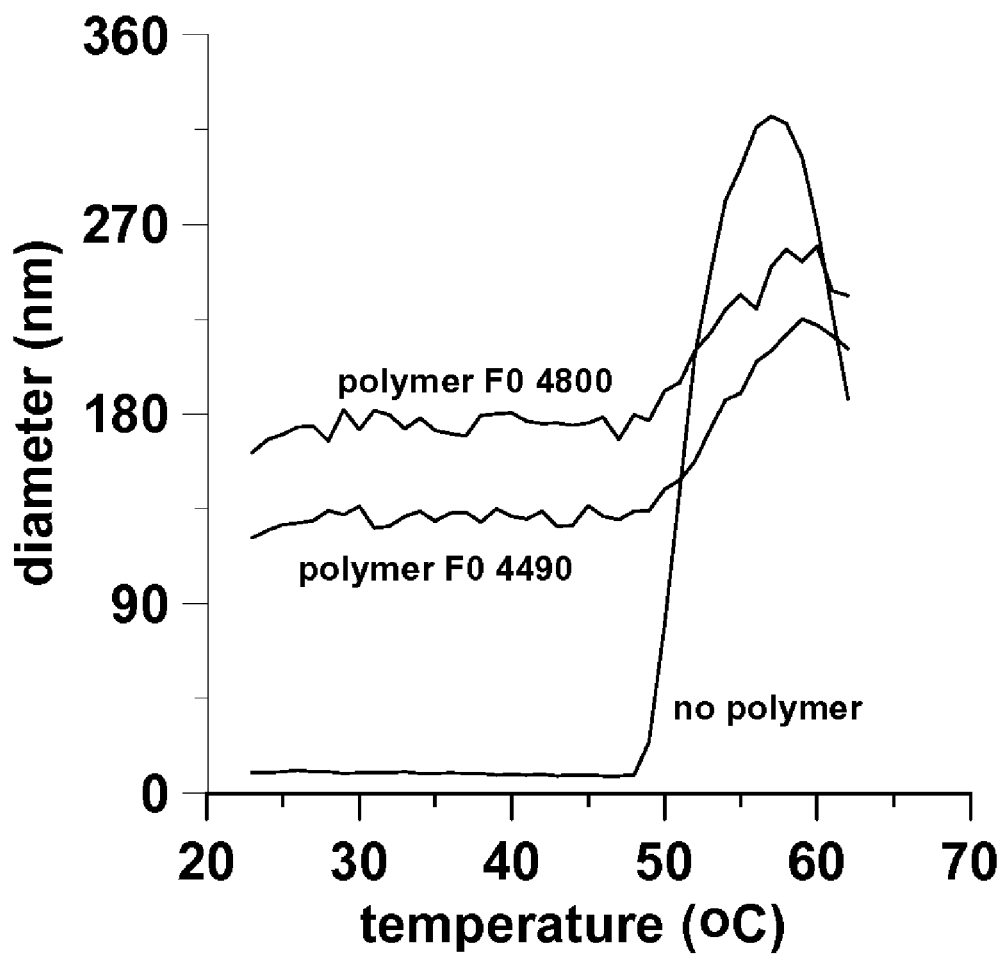
FIG. 10 demonstrates the thermal stabilization of enzyme in the presence of polymer.

The presence of c-PAM polymers retards the degradation of enzyme at elevated temperatures as illustrated by the results in FIG. 10. In this example, the particle diameter of the enzyme was measured with a Brookhaven 90Plus light scattering analyzer. In the absence of the polymer the particle diameter of the enzyme increases from about 10 nm and rises to about 300 nm as the enzyme denatures. The increase in diameter is caused by unfolding of the protein. In the presence of the polymers (FO4800 and FO4490 obtained from SNF Inc.) the initial particle diameter increases because the enzyme binds to the much larger polymer. It can be seen in FIG. 10 that the slope of the curve between about 50° C. and about 60° C. is much lower for the polymer-bound enzyme than the slope for the enzyme alone, i.e. in the absence of the polymer.

Another way to measure the temperature sensitivity of the enzyme is to measure the change in diameter with increasing temperature and to identify the point at which the change is maximal. These temperatures are listed in Table 1 for several polymers obtained from SNF Inc. The polymers increase in cationicity in moving from left to right in Table 1. It is clear that the temperature corresponding to the maximum rate increases with increasing cationicity of the polymer. As a result, the polymer partially stabilizes the enzyme at higher temperature. Put another way, there is less enzyme denatured on a proportional basis at higher temperature in the presence of the polymer, especially if the polymer is of high cationicity. This permits use of the enzyme at a higher temperature than would otherwise be possible. Since the rate of the enzymatic reaction increases with temperature, even a small enhancement of stability is highly beneficial.

TABLE 1

|  | Free enzyme | FO 4190 | FO 4490 | FO 4690 | FO 4800 |
|---|---|---|---|---|---|
| Temp (° C.) at max. rate of change | 51 | 52 | 53 | 54 | 57 |

What is claimed is:

1. A method for increasing the rate of hydrolysis of a polysaccharide comprising:
   providing a polysaccharide in an aqueous medium;
   mixing an enzyme and a polymer with the aqueous medium to form a substantially homogeneous mixture of the enzyme, the polymer, and the polysaccharide in the aqueous medium; and reacting the enzyme with the polysaccharide in the presence of the polymer to convert at least a portion of the polysaccharide into glucose, wherein the reaction rate of the enzyme with the polysaccharide in the presence of the polymer is greater than the reaction rate of the enzyme with the polysaccharide in the absence of the polymer, and the polymer comprises a cationic polymer which is present in said aqueous medium at a concentration less than effective to flocculate the polysaccharide.

2. The method of claim 1, wherein the polysaccharide comprises cellulose or a derivative thereof, and wherein the enzyme comprises a cellulase.

3. The method of claim 1, wherein the polysaccharide comprises a starch or a derivative thereof, and wherein the enzyme comprises an amylase.

4. The method of claim 1, wherein the polymer has a molecular weight of about 100,000 Da to about 20 million Da and a charge density of about 5% to about 95%.

5. The method of claim 4, wherein the cationic polymer comprises a cationic polyacrylamide.

6. The method of claim 1, wherein the enzyme is present in the aqueous medium at a concentration of about 0.001% to about 10%.

7. The method of claim 1, wherein the polymer is present at a concentration less than about 0.1%.

8. The method of claim 1, further comprising fermenting the at least a portion of the glucose to produce ethanol.

* * * * *